US00PP25081P2

(12) United States Plant Patent
Barends

(10) Patent No.: US PP25,081 P2
(45) Date of Patent: Nov. 18, 2014

(54) ***OSTEOSPERMUM* PLANT NAMED 'FIDOSTSUPWHI'**

(50) Latin Name: *Osteospermum ecklonis*
Varietal Denomination: Fidostsupwhi

(71) Applicant: Eveline Barends, De Lier (NL)

(72) Inventor: Eveline Barends, De Lier (NL)

(73) Assignee: Fides B.V., De Lier (NL)

( * ) Notice: Subject to any disclaimer, the term of this patent is extended or adjusted under 35 U.S.C. 154(b) by 126 days.

(21) Appl. No.: 13/694,548

(22) Filed: Dec. 12, 2012

(51) Int. Cl.
*A01H 5/00* (2006.01)

(52) U.S. Cl.
USPC ..... Plt./360

(58) Field of Classification Search
USPC ..... Plt./360
See application file for complete search history.

*Primary Examiner* — Susan McCormick Ewoldt
(74) *Attorney, Agent, or Firm* — C. A. Whealy

(57) ABSTRACT

A new and distinct cultivar of *Osteospermum* plant named 'Fidostsupwhi', characterized by its compact and mounding plant habit; freely branching growth habit; freely and early flowering habit; large single-type inflorescences with white-colored ray florets; and good garden performance.

1 Drawing Sheet

Botanical designation: *Osteospermum ecklonis.*
Cultivar denomination: 'FIDOSTSUPWHI'.

BACKGROUND OF THE INVENTION

The present invention relates to a new and distinct cultivar of *Osteospermum* plant, botanically known as *Osteospermum ecklonis*, and hereinafter referred to by the name 'Fidostsupwhi'.

The new *Osteospermum* plant is a product of a planned breeding program conducted by the Inventor in De Lier, The Netherlands. The objective of the program is to create and develop new compact *Osteospermum* plants that are freely branching with numerous inflorescences with unique and attractive ray and disc floret coloration.

The new *Osteospermum* plant originated from a cross-pollination by the Inventor in May, 2008 of a proprietary selection of *Osteospermum ecklonis* identified as code number O 45710, not patented, as the female, or seed, parent with a proprietary selection of *Osteospermum ecklonis* identified as code number O 67241, not patented, as the male, or pollen, parent. The new *Osteospermum* plant was discovered and selected by the Inventor as a single flowering plant within the progeny of the stated cross-pollination in a controlled greenhouse environment in De Lier, The Netherlands in October, 2008.

Asexual reproduction of the new *Osteospermum* plant by terminal cuttings in a controlled greenhouse environment in De Lier, The Netherlands since November, 2008 has shown that the unique features of this new *Osteospermum* plant are stable and reproduced true to type in successive generations.

SUMMARY OF THE INVENTION

Plants of the new *Osteospermum* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fidostsupwhi'. These characteristics in combination distinguish 'Fidostsupwhi' as a new and distinct *Osteospermum* plant:

1. Compact and mounding plant habit.
2. Freely branching growth habit.
3. Freely and early flowering habit.
4. Large single-type inflorescences with white-colored ray florets.
5. Good garden performance.

Plants of the new *Osteospermum* differ primarily from plants of the female parent selection in ray floret color as plants of the female parent selection have bronze-colored ray florets. Plants of the new *Osteospermum* differ primarily from plants of the male parent selection in plant habit as plants of the new *Osteospermum* are more uniform than plants of the male parent selection.

Plants of the new *Osteospermum* can be compared to plants of the *Osteospermum* 'Fidostwhi', disclosed in U.S. Plant Pat. No. 20,548. In side-by-side comparisons conducted in De Lier, The Netherlands, plants of the new *Osteospermum* differed primarily from plants of 'Fidostwhi' in growth habit as plants of the new *Osteospermum* were more vigorous than plants of 'Fidostwhi'. In addition, plants of the new *Osteospermum* have larger inflorescences than plants of 'Fidostwhi'.

BRIEF DESCRIPTION OF THE PHOTOGRAPH

The accompanying photograph illustrates the overall appearance of the new *Osteospermum* plant showing the colors as true as it is reasonably possible to obtain in colored reproductions of this type. Colors in the photograph may differ slightly from the color values cited in the detailed botanical description which accurately describe the colors of the new *Osteospermum* plant.

The photograph comprises a side perspective view of a typical flowering plant of 'Fidostsupwhi' grown in a container.

DETAILED BOTANICAL DESCRIPTION

The aforementioned photograph, following observations and measurements describe plants grown during the spring and early summer in 13-cm containers in a glass-covered greenhouse in De Lier, The Netherlands and under cultural practices typical of commercial *Osteospermum* production. During the production of the plants, day temperatures ranged from 17° C. to 35° C. and night temperatures ranged from 15° C. to 25° C. Plants were pinched one time and were 13 weeks old when the photograph and description were taken. In the following description, color references are made to The Royal Horticultural Society Colour Chart, 2007 Edition, except where general terms of ordinary dictionary significance are used.

Botanical classification: *Osteospermum ecklonis* 'Fidostsupwhi'.

Parentage:

*Female, or seed, parent*.—Proprietary selection of *Osteospermum ecklonis* identified as code number O 45710, not patented.

*Male, or pollen, parent*.—Proprietary selection of *Osteospermum ecklonis* identified as code number O 67241, not patented.

Propagation:

*Type*.—Terminal vegetative cuttings.

*Time to initiate roots, summer*.—About six days at 22° C.

*Time to initiate roots, winter*.—About seven days at 22° C.

*Time to produce a rooted cutting, summer*.—About twelve days at 22° C. to 30° C.

*Time to produce a rooted cutting, winter*.—About 14 days at 20° C. to 25° C.

*Root description*.—Medium in thickness, fibrous; whitish grey in color.

*Rooting habit*.—Moderately freely branching; medium density.

Plant description:

*Plant form and growth habit*.—Compact and mounding plant habit; relatively short internodes, dense and bushy growth habit; moderately vigorous growth habit.

*Plant height*.—About 14 cm.

*Plant diameter*.—About 22 cm.

*Lateral branches*.—Quantity per plant: Freely branching habit, about five lateral branches develop per plant; pinching enhances lateral branch development. Length: About 14 cm to 16 cm. Diameter: About 5 mm. Internode length: About 1 cm to 3.5 cm. Strength: Strong, sturdy. Texture: Sparsely pubescent. Color: Close to 144C.

*Foliage description*.—Arrangement: Alternate, simple; sessile. Length: About 6 cm to 9 cm. Width: About 2.5 cm to 4 cm. Shape: Elliptic. Apex: Acute. Base: Attenuate. Margin: Lobed; serrate. Texture, upper surface: Smooth, glabrous. Texture, lower surface: Sparsely pubescent. Venation pattern: Pinnate. Color: Developing leaves, upper surface: Close to N137B. Developing leaves, lower surface: Close to 137B. Fully expanded leaves, upper surface: Close to N137A; venation, close to 144B. Fully expanded leaves, lower surface: Close to 137B; venation, close to 144B.

Inflorescence description:

*Appearance and aspect*.—Terminal and axillary inflorescences; inflorescences positioned beyond the foliar plane on moderately strong peduncles and face mostly upright; single-type inflorescence form with elliptic to slightly obovate-shaped ray florets and tubular disc florets; ray and disc florets developing acropetally on a capitulum.

*Flowering habit*.—Freely flowering habit; about 10 to 40 inflorescences developing per plant.

*Fragrance*.—None detected.

*Flowering response*.—In The Netherlands, plants of the new *Osteospermum* flower continuously from spring until first frost in the autumn; early flowering habit, plants begin flowering about eight weeks after planting.

*Inflorescence longevity*.—At temperatures of 14° C. to 20° C., inflorescences last about 2.5 weeks on the plant; inflorescences persistent.

*Inflorescence buds, just prior to anthesis*.—Height: About 1.8 cm. Diameter: About 1.2 cm. Shape: Globular to ovoid. Color: Close to 137C.

*Inflorescence size*.—Diameter: About 7.5 cm. Depth (height): About 1 cm. Disc diameter: About 1.2 cm to 1.5 cm. Receptacle diameter: About 4 mm. Receptacle height: About 4 mm. Receptacle color: Close to 146A.

*Ray florets*.—Length: About 3.5 cm to 3.7 cm. Width: About 9 mm. Shape: Elliptic to slightly obovate. Apex: Rounded to slightly obtuse. Base: Attenuate. Margin: Entire. Texture, upper and lower surfaces: Smooth, glabrous; satiny. Quantity per inflorescence and arrangement: About 22 to 26 in one to two whorls. Color: When opening and fully opened, upper surface: Close to N155D; color does not fade with development. When opening and fully opened, lower surface: Close to N155D; longitudinal stripes, close to 90B; color does not fade with development.

*Disc florets*.—Shape: Tubular with five pointed apices. Length: About 5 mm. Diameter: About 1 mm. Number of disc florets per inflorescence: About 60 to 70. Color, immature: Apex and mid-section: Close to 71A. Base: Close to 77D. Color, mature: Apex and mid-section: Close to 71B. Base: Close to 77D.

*Phyllaries*.—Quantity per inflorescence and arrangement: About 12 to 14 in a single whorl. Length: About 8 mm to 9 mm. Width: About 1 mm to 2 mm. Shape: Lanceolate. Apex: Acuminate. Base: Truncate. Margin: Entire. Texture, upper and lower surfaces: Sparsely pubescent. Color, upper surface: Close to 146A. Color, lower surface: Close to 138A.

*Peduncles*.—Length: About 10 cm to 11 cm. Diameter: About 2 mm. Strength: Moderately strong. Aspect: Mostly upright. Texture: Pubescent. Color: Close to 144A.

*Reproductive organs*.—Androecium: Present on disc florets only. Anther shape: Lanceolate. Anther length: About 2 mm. Anther color: Close to N77A. Pollen amount: Moderate to abundant. Pollen color: Close to 23A. Gynoecium: Present on both ray and disc florets. Pistil length: About 8 mm. Stigma shape: Bi-parted. Stigma color: Close to 79A. Style length: About 6 mm. Style color: Close to 79A Ovary color: Close to N155D.

*Seeds and fruits*.—Seed and fruit development have not been observed on plants of the new *Osteospermum*.

Disease & pest resistance: Plants of the new *Osteospermum* have not been observed to be resistant to pathogens and pests common to *Osteospermum* plants.

Garden performance: Plants of the new *Osteospermum* have been observed to have good garden performance and to tolerate rain, wind and temperatures ranging from about 4° C. to about 35° C.

It is claimed:

1. A new and distinct *Osteospermum* plant named 'Fidostsupwhi' as illustrated and described.

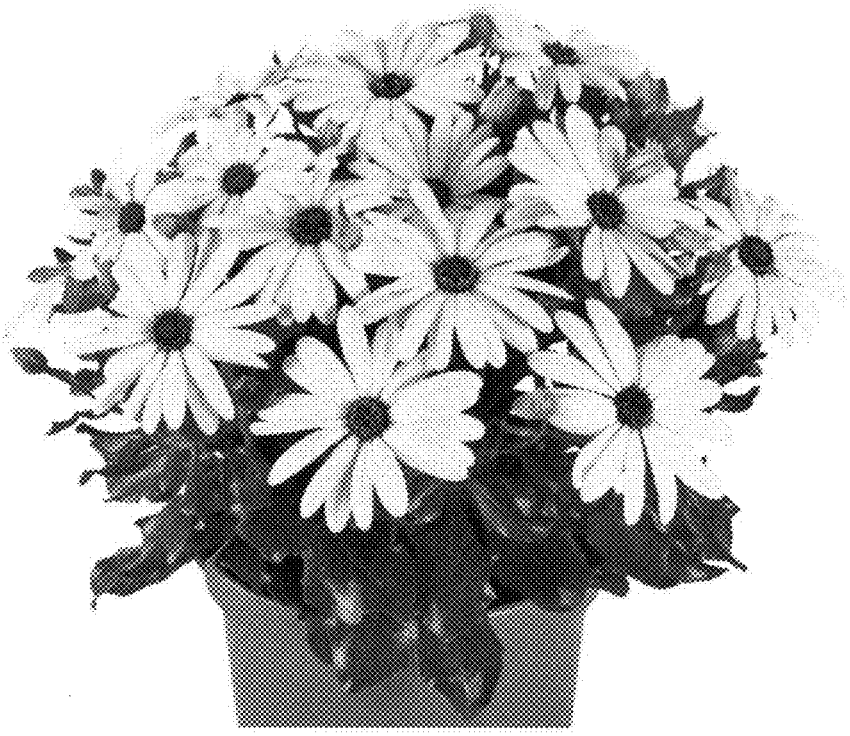

* * * * *